United States Patent
Chambers et al.

(10) Patent No.: US 6,441,232 B1
(45) Date of Patent: Aug. 27, 2002

(54) SELECTIVE NITROGEN FUNCTIONALIZATION OF ORGANIC COMPOUNDS

(75) Inventors: Richard Dickinson Chambers; Mandy Parsons; Graham Sandford, all of Durham (GB)

(73) Assignee: F2 Chemicals Ltd. (GB)

( * ) Notice: Subject to any disclaimer, the term of this patent is extended or adjusted under 35 U.S.C. 154(b) by 0 days.

(21) Appl. No.: 09/936,593

(22) PCT Filed: Jan. 11, 2001

(86) PCT No.: PCT/GB01/00111

§ 371 (c)(1),
(2), (4) Date: Jan. 1, 2002

(87) PCT Pub. No.: WO01/53234

PCT Pub. Date: Jul. 26, 2001

(30) Foreign Application Priority Data

Jan. 19, 2000 (GB) .............................................. 0001093

(51) Int. Cl.[7] ............................................ C07C 231/06
(52) U.S. Cl. ...................... 564/124; 564/188; 564/189; 564/215; 564/217
(58) Field of Search ............................... 564/124, 215, 564/217, 188, 189

(56) References Cited

U.S. PATENT DOCUMENTS 4,808,628 A * 2/1989 Shepherd et al. ............ 514/513
5,712,413 A * 1/1998 Burrington et al. .......... 564/131

FOREIGN PATENT DOCUMENTS

WO 00/58241 10/2000

OTHER PUBLICATIONS

Journal of the American Chemical Society, 101:15, Jul. 18, 1979, pp. 4416–4417 Mechanism of the Oxidation of Alkanes with Nitronium Tetrafluoroborate in Acetonitrile. Evidence for a Carbenium Ion Intermediate.

Journal of the American Chemical Society, J. Org. Chem. 1980, vol. 45, pp. 165–167 Reactions of Nitrosonium Tetrafluoroborate in Acetonitrile with Organic Molecules Containing Nonbonding Electrons. Synthesis of Acetamides.

Journal of the American Chemical Society, J. Org. chem. 1980, vol. 45, pp. 3532–3533 Synthetic Methods and reactions. Novel Synthesis of N–(1–Adamantyl)amides from Adamantane.

Synthesis Nov. 1992, No. 11, pp. 1090–1092, Aluminium Chloride/Dichloromethane (Chloroform) Induced Carbonylation, Ritter Reaction, and Cyanation of Adamantane.

Journal of the American Chemical Society, Acc. Chem. Res. 1992, vol. 25, pp. 504–512 The Selective Functionalization of Saturated Hydrocarbons: Gif Chemistry.

Journal of the American Chemical Society, Acc. Chem. Res. 1987, vol. 20, pp. 422–428 Electrophilic Methanr Conversion.

Science, vol. 280, Apr. 1998, pp. 560–564 Platinum Catalysts for the High–Yield Oxidation of Methane to a Methanol Derivative.

Journal of the American Chemical Society, 1996, vol. 118, pp. 8961–8962 Rapid Catalytic Oxygenation of Hydrocarbons by Ruthenium Pentafluorophenylporphyrin Complexes: Evidence for the Involvement of a Ru(III) Intermediate.

Journal of the American Chemical Society, 1997, vol. 119, pp. 4535–4536 Selective Catalytic Hydroxylation of a Steroid by an Artificial Cytochrome P–450 Enzyme.

Journal of the American Chemical Society, 1971, pp. 1259–1261 Electrophilic Reactions at Single Bonds. Nitration and Nitrolysis of Alkanes and Cycloalkanes with Nitronium Salts.

New Journal of Chemistry, vol. 13, 1989, pp. 651–657 Animation of Alkanes Catalyzed by Iron and Manganese–Porphyrins: Particular Selectivity for Oxidations of Linear Alkanes.

* cited by examiner

Primary Examiner—Shailendra Kumar
(74) Attorney, Agent, or Firm—Reising, Ethington, Barnes, Kisselle, Learman & McCulloch, P.C.

(57) ABSTRACT

There is provided a method of selectively replacing a carbon-hydrogen bond at an unactivated saturated sp3 hybridised carbon atom in an organic compound by a carbon-nitrogen bond, the method comprising reacting the compound with a fluorinating agent in a solvent reaction medium comprising a nitrile compound and providing a Lewis acid whereby the carbon-hydrogen bond is replaced by a carbon-nitrogen bond. Advantageously, the reaction may be performed in one stage and/or in one vessel. Advantageously, the method may be carried out at or just below ambient or room temperature.

10 Claims, No Drawings

SELECTIVE NITROGEN FUNCTIONALIZATION OF ORGANIC COMPOUNDS

This application is a 371 of PCT/GB01/00111, filed Jan. 11, 2001.

The invention relates to a method for the selective replacement of a carbon-hydrogen bond at an unactivated, saturated sp3 carbon atom in an organic compound by a carbon-nitrogen bond.

The search for efficient methodology for the selective conversion of alkanes to functionalised derivatives has been the focus of substantial effort from many research groups worldwide over the last 20 years (C. L. Hill, Eds., *Activation and Functionalisation of Alkanes*, Wiley, New York, 1989). Alkanes constitute roughly half of the mass of crude oil and, therefore, a vast resource of raw material is potentially available for chemical synthesis but, at present, most of the world's alkane resources are simply burnt to provide heat and energy or, in the case of the lower alkanes, destroyed at the point of extraction.

Effective processes for the transformation of hydrocarbons to functionalised derivatives are urgently required and many approaches have been investigated in attempts to put the earth's fossil fuels to better use. Potential solutions to carbon-hydrogen bond activation have included use of the Gif/GoAgg oxidation method (typically comprising mixtures of iron, pyridine, acetic acid and hydrogen peroxide) devised by Barton (D. H. R. Barton and D. Doller, *Acc Chem. Res.*, 1992, 25, 504), use of highly electrophilic reagents or superacids by Olah (G. A. Olah. *Acc. Chem. Res.*, 1987,20,422), use of transition metal catalysts (R. A. Periana, D. J. Taube, S. Gamble, H. Taube, T. Satoh and H Fujii, *Science*, 1998, 280, 560), use of metalloporphyrin catalysts (J. T. Groves, M. Bonchio, T. Carofiglio and K. Shalyaev, *J. Am. Chem. Soc.*, 118,8961), use of enzymatic (Cytochrome P-450) and use of biomimetic oxidation procedures (R. Breslow, X. Zhang and Y. Huang, *J. Am. Chem. Soc.*, 1997. 119, 4535). However, low yields, long reaction times, lack of selectively and high expense, limit the use of many of these approaches. In general, the functionalised alkane products are typically more reactive than the alkane starting materials and so reactions must be carried out to very low conversion in order to minimise by-product formation.

Halogenation processes, most commonly using molecular chlorine, have been intensively studied (Olah, *Hydrocarbon Chemistry*, John Wiley and Sons 1995). Both thermal and photochemical chlorination processes are well established and are usually operated at high temperature (>300° C.) in the vapour phase. However, due to the harsh reaction environment, free radical chlorination of hydrocarbons is, in general, a totally non-selective process and gives all possible monochlorinated products limiting the utility of this methodology.

The transformation of unactivated sp3 hybridised carbon-hydrogen bonds in saturated systems to carbon-nitrogen bonds, i.e. nitrogen functionalisation, represents a significant synthetic challenge. Nitration of alkanes (Olah,*J. Am. Chem. Soc.*, 1971, 93, 1259) can be accomplished using nitronium tetrafluoroborate in superacidic solution but carbon-carbon bond cleavage is a significant competing process which leads to low yields of nitro-alkane derivatives. Amination of alkanes (Mahy, *New. J. Chem.*, 1989, 13, 651) has been achieved using porphyrin catalysed reaction of tosylimidoiodobenzene to give tosylamino-hydrocarbon products. The use of harsh reaction conditions, high expense and low efficiency precludes the use of these processes on a large scale.

It is an object of the invention to provide a method of transforming unactivated sp3 hybridised carbon-hydrogen bonds to carbon-nitrogen bonds in which the aforementioned problems are reduced or eliminated.

According to the invention there is provided a method of selectively replacing a carbon-hydrogen bond at an unactivated saturated sp3 hybridised carbon atom in an organic compound by a carbon-nitrogen bond, the method comprising reacting the compound with a fluorinating agent in a solvent reaction medium comprising a nitrile compound and providing a Lewis acid whereby the carbon-hydrogen bond is replaced by a carbon-nitrogen bond.

Advantageously, the present invention provides a method for transforming unactivated sp3 hybridised carbon-hydrogen bonds to carbon-nitrogen bonds, i.e. nitrogen functionalisation, by a high yielding, economically feasible process.

Advantageously, the reaction may be carried out using readily available and inexpensive reagents.

Advantageously, the reaction may be performed in one stage and/or in one vessel.

Advantageously, the method may be carried out at or just below ambient or room temperature.

Accordingly, the invention provides a significant improvement in direct selective nitrogen functionalisation processes over the prior art.

The term unactivated saturated sp3 carbon atom used herein means a saturated sp3 hybridised carbon atom not directly bonded to any functional group. That is to say, any carbon atom which is part of a functional group (e.g. carbonyl C=O) or is bearing a functional group (e.g. C—OH) must be at least two atoms distant from the carbon which is bonded to the hydrogen atom that is replaced by a nitrogen atom. In the prior art, functional groups such as for example carbonyl were directly bonded, i.e. less than two carbons distant, to the carbon atom which is bonded to the hydrogen atom that is replaced. Thus, in the prior art, the functional group would activate the carbon-hydrogen bond on the saturated carbon atom.

Preferably, the fluorinating agent comprises elemental fluorine gas. Fluorine gas is readily available and cheap.

Preferably the fluorine gas is diluted before use by mixing with an inert gas such as helium or nitrogen. The concentration of fluorine in the inert gas may be from 1% to 50% by volume, preferably from 2% to 25% by volume and especially from 5% to 15% by volume.

The ratio of fluorine gas to organic compound to be fluorinated may be varied within wide limits although it is preferred that the molar ratio is in the range 0.5 to 10:1 and more preferred that is 1 to 3:1.

The invention may be carried out by passing fluorine gas into a mixture containing the organic compound, the Lewis acid and the nitrile containing solvent in a suitable vessel. To ensure complete conversion of substrate to the corresponding N-functionalised derivative the reaction mixture can, if necessary, be heated externally, to a temperature ranging from 30° C. to 80° C., preferably 50–60° C., after the passage of fluorine gas. Alternatively, a flowing stream of the mixture may be contacted with a gaseous flow of fluorine in counter current or co-current fashion.

Alternatively, the invention may be carried out by passing elemental fluorine gas into a mixture containing the organic compound and the nitrile containing solvent in a suitable vessel. After passage of the fluorine, the Lewis acid, preferably boron trifluoride, is added to the reaction mixture at room temperature and stirred. A flowing stream of the mixture may be contacted with a gaseous flow of fluorine in counter-current or co-current fashion.

Alternatively, the invention may be carried out using a fluorinating agent which comprises a compound containing an N—F bond. The fluorinating agent may, in particular, comprise one of the following: an N-fluoropiperidine, an N-fluoropyridone, an N-fluorosulphonamide, an N-fluoropyridinium salt, an N-fluoroimide or an N-fluorodiazabicycloalkane or similar reagents. When an N—F fluorinating reagent is used, the invention may be carried out by heating a mixture consisting of the N—F fluorinating reagent, the substrate, a Lewis acid as required and the nitrile containing solvent in a suitable vessel. The compound containing an N—F bond may itself provide the Lewis acid.

Where the fluorinating agent comprises a compound containing an N—F bond, preferably, the fluorinating agent comprises an N-fluorinated diazoniabicycloalkane, i.e. one of the class of reagents known commercially as Selectfluor (Trade mark) reagents. In such cases, more preferably the fluorinating agent is an N-fluorinated 1,4,diazoniabicyclo-(2.2.2) octane derivative and most preferably the fluorinating agent is a 1-alkyl-4-fluor 1,4-diazoniabicyclo (2,2,2) octane salt, particularly a 1-chloromethyl-4-fluoro-1,4-diazabicyclo(2,2,2)octane salt. Preferably, the salt in such cases is a bis (tetrafluoroborate) salt.

Selectfluor (Trade mark) reagents have been described previously in detail, for example, in U.S. Pat. No. 5,442,084. Known preferred substituents, counter-ions and other features of Selectfluor (Trade mark) reagents are incorporated herein by reference. In particular, there is incorporated herein by reference those features described in U.S. Pat. No. 5,422,084 at column 3 lines 11 to 25 and at column 5 line 36 to column 7 line 10.

Any suitable Lewis acid may be used. Preferably, the Lewis acid comprises boron trifluoride. The ratio of the Lewis acid to the organic compound, e.g. of formula 1,5 and 6 below, may be varied within wide limits although it is preferred that the molar ratio is in the range 0.5 to 10:1, especially 1 to 4:1. The Lewis acid may be present in the solvent at the time of reacting the compound with the fluorinating agent or it may be added after reacting with the fluorinating agent.

The fluorination reaction is conducted in a solvent comprising a nitrile compound, i.e. a compound which bears a nitrile functional group. Preferably, the nitrile is acetonitrile, or propionitrile. Most preferably, the nitrile is acetonitrile. Preferably, the solvent substantially comprises a nitrile compound. The solvent may consist entirely or almost entirely of a nitrile compound.

The reaction of the process where elemental fluorine is uses as the fluorinating reagent may be carried out at a temperature in the range $-60°$ C. to $+150°$ C., although a temperature of from $0°$ C. to $+30°$ C. is preferred. The reaction of the process where an N—F fluorinating agent is used may also be carried out of a temperature in the range $-60°$ C. to $+150°$ C., although a temperature of from $+50°$ C. to $+110°$ C. is preferred.

The present invention, for example, provides a method for the preparation of a selectively functionalised organic compound 2, by reaction of a precursor 1, with fluorine gas in the presence of a Lewis acid such as boron trifluoride or an N—F fluorinating agent and an organic compound bearing a nitrile functional group such as acetonitrile, followed by an aqueous work-up. $R_1$ to $R_4$ are as defined below.

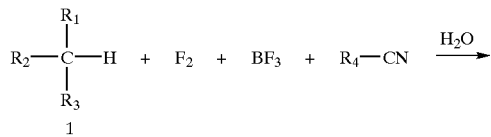

1

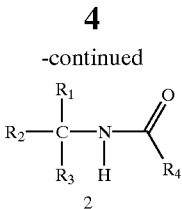

2

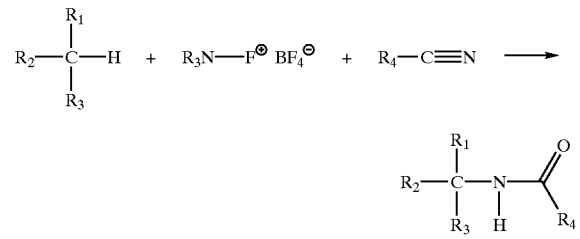

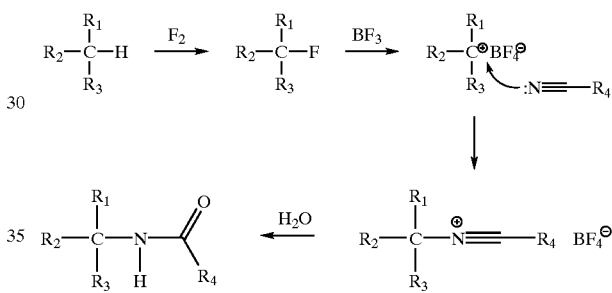

The believed mechanism of the reaction is outlined below but should be understood not to limit the invention in any way. Initial reaction of 1 with elemental fluorine leads to a selectively fluorinated product which ionises in the presence of boron trifluoride and hydrogen fluoride to give an intermediate carbocationic species. The carbocation then reacts with the nitrile which yields 2 after aqueous work-up.

The invention provides a method for preparing a wide range of selectively functionalised organic compounds, for example, compounds 2,3 and 4, comprising converting the corresponding precursor compounds 1,5 and 6 as follows:

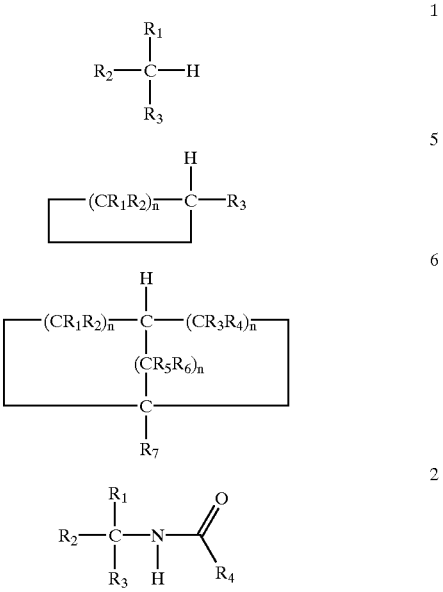

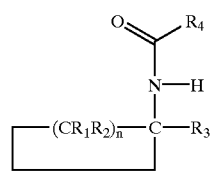

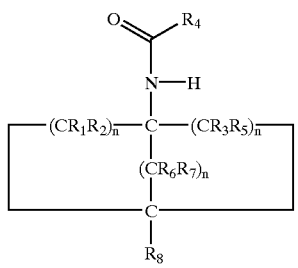

In structures 2,3,4 and 1,5,6, the groups $R_1$, $R_2$, $R_3$, $R_4$, $R_5$, $R_6$ and $R_7$ may be independently selected from hydrogen, alkyl, substituted alkyl, cycloalkyl, substituted cycloalkyl, aryl, substituted aryl, etc. Where any of the groups $R_1$, $R_2$, $R_3$, $R_4$, $R_5$, $R_6$ and $R_7$ is an alkyl, cycloakyl or aryl substitutent, the said group may include one or more optional substituents or hetero-atoms.

The structures represented by formulae 3,4,5 and 6 are cyclic and the n values are independently integers in the inclusive range from 1 to 8.

When the amidation reaction of the process is complete, the selectively functionalised organic compounds 2,3 and 4 may be isolated by purging the reaction mixture with an inert gas to remove any residual fluorine gas or hydrogen fluoride formed during the reaction, followed by dilution with water and extraction of the selectively functionalised organic compound into a suitable solvent followed by purification by distillation, column chromatography or recrystallisation.

The saturated sp3 hybridised carbon atom may be bonded to three other carbon atoms and a hydrogen atom, i.e. a tertiary carbon atom. The saturated sp3 hybridised carbon atom may be bonded to two other carbon atoms and two hydrogen atoms, i.e. a secondary carbon atom.

The saturated carbon atom may form part of a cyclic structure, e.g. a saturated tertiary carbon atom may form part of a cyclic structure such as decalin or adamantane. Where the saturated carbon atom is a secondary carbon atom it too may form part of a cyclic structure.

Specific embodiments of the invention will now be described, by way of example only, with reference to the following example.

METHOD 1

EXAMPLE 1

Functionalisation of Adamantane

Elemental fluorine (208 mmol) as a 10% (v/v) mixture with nitrogen was passed through a stirred, cooled (0° C.) mixture of adamantane (7.07 g, 52 mmol) and dry acetonitrile (140 cm$^3$). After addition of the fluorine, boron trifluoride etherate (29.54 g, 208 mmol) was added to the reaction mixture and after 5 min. of stirring at room temperature the reaction mixture was poured into water, neutralised (NaHCO$_3$) and extracted using dichloromethane. The combined dried (MgSO$_4$) organic extracts were evaporated to give a brown crude product mixture which, upon recrystallisation from acetonitrile, gave, N-(1-adamantyl) acetamide (5.25 g, 74%, 70% conv.) as a white solid; mp 150–151° C. (Found: C,74.55; H,9.9; N, 7.3.C$_{12}$H$_{19}$NO requires C, 74.55; H,9.9; N,7.3%); $\delta_h$ 400 MHz) 1.66 (6 H,s,4-H), 1.89 (3 H, s, CH$_3$), 1.97 (6 H, s, 2-H), 2.05 (3H, m, 3-H), 5.20 (1 H, br s, NH); $\delta_c$ (101 MHz) 24.7 (s, CH$_3$), 29.4 (s,C-3), 36.3 (s, C-4), 41.6 (s, C-2), 51.8 (s, C-1), 169.3 (s, CO), m/z (EI$^+$) 193 (M$^+$, 100%), 178 (24, M$^+$—CH$_3$), 150 (18, M$^+$—COCH$_3$).

METHOD 2

EXAMPLE 2

Functionalisation of Adamantane

Elemental fluorine (28 mmol) as a 10% (v/v) mixture with nitrogen was passed through a stirred, cooled (0° C.) mixture of adamantane (1.50 g, 11 mmol) boron trifluoride etherate (24.57 g, 173 mmol) and dry acetonitrile (140 cm$^3$). After addition of the fluorine, the reaction mixture was poured into water, neutralised (NaHCO$_3$) and extracted using dichloromethane. The combined dried (MgSO$_4$) organic extracts were evaporated to give a dark yellow solid (1.52 g) which contained adamantane (61 area %), N-(1-adamantyl) acetamide (26 area %); data as above, and a small number of unidentified products.

EXAMPLE 3

Functionalisation of Cyclohexane

Using a similar procedure to that described above (Method 2), cyclohexane (9.8 g, 117 mmol), elemental fluorine (59 mmol), boron trifluoride etherate (16.6 g, 117 mmol), and anhydrous acetonitrile (120 cm$^3$) gave, after heating (65° C.) and the work-up as detailed above, a crude product mixture which was distilled to give cyclohexane (4.6 g, 55 mmol); bp 67° C. The brown solid which remained gave, after recrystallisation, N-(cyclohexyl)acetamide (4.5 g, 51%, 53% conv.) as a white solid; mp 104–105° C. (from acetonitrile) (Found: M$^+$, 141.1153 C$_8$H$_{15}$NO requires: M$^+$, 141.1153); $\delta_H$ (400 MHz) 1.06–1.20 (3 H, m, CH$_2$), 1.28 (2 H, m, CH$_2$), 1.55–1.73 (3 H, m, CH$_2$), 1.85 (2 H, m, CH$_2$), 1.94 (3 H, s, CH$_3$), 3.74 (1 H, m, H-1), 5.43 (1 H, br s, NH); $\delta_C$ (101 MHz) 23.6 (s, CH$_3$), 24.8 (s, C-2 or C-3 or C-4), 25.5 (s, C-2 or C-3 or C-4), 33.2 (s, C-2 or C-3 or C-4), 48.1 (s, C-1), 169.0 (s, CO); m/z (EI$^+$) 141 (M$^+$, 8%), 98 (4, M$^{+-}$COCH$_3$), 70 (6), 60 (58).

EXAMPLE 4

Functionalisation of cis-Decalin

Using a similar procedure to that described above (Method 2), cis-decalin (2.2 g, 16 mmol), elemental fluorine (65 mmol), boron trifluoride etherate (2.3 g, 16 mmol), and anhydrous acetonitrile (120 cm$^3$) gave, after heating (82° C.) and the work-up as detailed above, a crude product mixture which was distilled to give decalin (0.7 g, 5 mmol); bp 55° C./10 mmHg. The brown solid which remained gave, after recrystallisation, N-(trans-9-decalyl)acetamide (0.8 g, 49%, 67% conv.) as a white solid; mp 183–184° C. (from acetonitrile) (Found C, 73.6; H, 10.9; N, 7.3. C$_{12}$H$_{21}$NO requires: C, 73.8; H, 10.9; N, 7.2%); $\delta_H$ (400 MHz) 0.85–1.68 (18 H, m), 2.57 (1 H, s), 2.62 (1 H, s), 4.89 (1 H, br s, NH); $\delta_C$ (101 MHz) 21.6 (s, CH$_2$), 24.6 (s, CH$_3$), 26.1 (s, CH$_2$), 28.6 (s, CH$_2$), 34.4 (s, CH$_2$), 45.2 (s, CH), 55.9 (CNHCO), 169.2 (s, CO); m/z (EI$^+$) 195 (M$^+$, 1%), 152 (18), 136 (100), 121 (141).

EXAMPLE 5

Functionalisation of trans-Decalin

Using a similar procedure to that described above (Method 2), trans-decalin (3.0 g, 22 mmol), elemental fluorine (44 mmol), boron trifluoride etherate (3.1 g, 22 mmol), and anhydrous acetonitrile (120 cm$^3$) gave, after heating (82° C.) and the work-up as detailed above, a crude product mixture which was distilled to give decalin (1.5 g, 11 mmol); bp 50° C./8 mmHg. The brown solid which remained gave, after recrystallisation, N-(trans-9-decalyl) acetamide (1.0 g, 45%, 49% conv.) as a white solid; spectral and physical data as described in Example 3.

EXAMPLE 6

Functionalisation of Norbornane

Using a similar procedure to that described above (Method 2), norbornane (2.4 g, 25 mmol), elemental fluorine (59 mmol), boron trifluoride etherate (3.6 g, 25 mmol), and anhydrous acetonitrile (120 cm$^3$) gave a reaction mixture which was poured into water, neutralised (NaHCO$_3$) and filtered to remove norbornane (1.0 g, 10 mmol). The liquid which remained was worked up as above and gave, after recrystallisation, N-(exo-2-norbornyl)acetamide (1.0 g, 45%, 60% conv.) as a white solid; 141–142° C. (from acetonitrile) (Found C, 70.2; H, 10.2; N, 9.3. C$_9$H$_{15}$NO requires: C, 70.5; H, 9.9; N, 9.2%); $\delta_H$ (400 MHz) 1.08–1.55 (7 H, m), 1.80 (1 H, m, 3-H), 1.94 (3 H, s, CH$_3$), 2.19 (1 H, m, 1-H), 2.27 (1 H, m, 4-H), 3.71 (1 H, m), 5.35 (1 H, br s, NH); $\delta_C$ (100 MHz) 23.8 (s, CH$_3$), 26.4 (s, C-6), 27.1 (s, C-5), 35.6 (s, C-7), 35.7 (s, C-4), 40.5 (s, C-3), 42.3 (s, C-1), 52.8 (s, C-2), 169.4 (s, CO); m/z (EI$^+$) 193 (M$^+$, 75%), 138 (21, M$^{+-}$CH$_3$), 124 (23), 94 (100).

METHOD 3

EXAMPLE 7

Functionalisation of Adamantane Mediated by an N—F Electrophilic Fluorinating Agent [Selectfluor (Trade Mark)]

A mixture consisting of adamantane (2.0 g, 15 mmol), Selectfluor™ (13.5 g, 38 mmol), and anhydrous acetonitrile (120 cm$^3$) was stirred and heated (82° C.) then poured into water (70 cm$^3$), neutralised (NaHCO$_3$) and extracted with DCM (3×40 cm$^3$). The combined organic extracts were dried (MgSO$_4$) and evaporated to leave the crude product mixture (2.3 g) which, by GC/MS analysis, contained 1-fluoroadamantane (10%), difluoroadamantane (2%); m/z (EI$^+$) 172 (M$^+$, 48%), 152 (77, M$^{+-}$HF), N-(1-adamantyl) acetamide (51%), N-(2-adamantyl)acetamide (13 %); m/z (EI$^+$) 193 (M$^+$, 50%), 178 (10, M$^+$-CH$_3$), 150 (16, M$^+$-COCH$_3$) and unidentified products. Purification of the mixture by column chromatography on silica gel using 1:1 DCM-methanol as the eluent gave N-(1-adamantyl) acetamide (0.7 g, 25%, 93% conv.); physical and spectral data as above.

What is claimed is:

1. A method of selectively replacing a carbon-hydrogen bond at an unactivated saturated Sp$^3$ hybridised carbon atom in an organic compound by a carbon-nitrogen bond, the method comprising reacting the compound with a fluorinating agent in a solvent reaction medium comprising a nitrile compound and providing a Lewis acid whereby the carbon-hydrogen bond is replaced by a carbon-nitrogen bond.

2. A method according to claim 1 wherein the fluorinating agent comprises elemental fluorine.

3. A method according to claim 1 wherein the fluorinating agent comprises a compound containing an N—F bond.

4. A method according to any one preceding claim wherein the nitrile compound is selected from acetonitrile and propionitrile.

5. A method according to one preceding claim wherein the solvent reaction medium mainly comprises nitrile compound.

6. A method according to any one preceding claim wherein the Lewis acid comprises boron trifluoride.

7. A method according to any one preceding claim wherein the molar ratio of the Lewis acid to the organic compound is in the range from 0.5:1 to 10:1.

8. A method according to claim 7 wherein the molar ratio of the Lewis acid to the organic compound is in the range from 1:1 to 4:1.

9. A method according to any one preceding claim wherein the Lewis acid is added to the solvent reaction medium after reacting the compound with the fluorinating agent.

10. A method according to any preceding claim wherein the organic compound is selected from the group consisting of compounds 1,5 and 6 as follows:

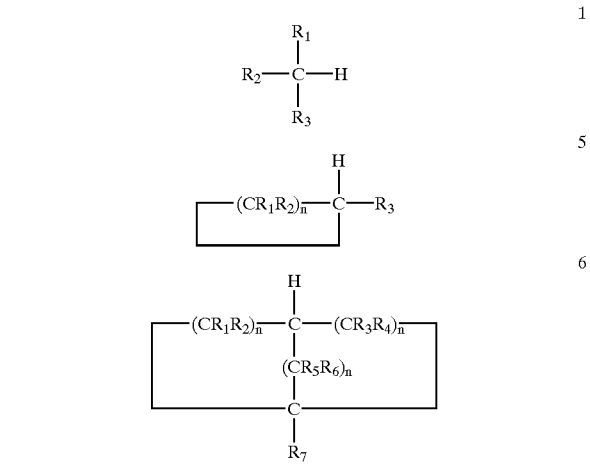

and whereby the replacement by a carbon-nitrogen bond produces the corresponding compound 2,3 or 4 as follows:

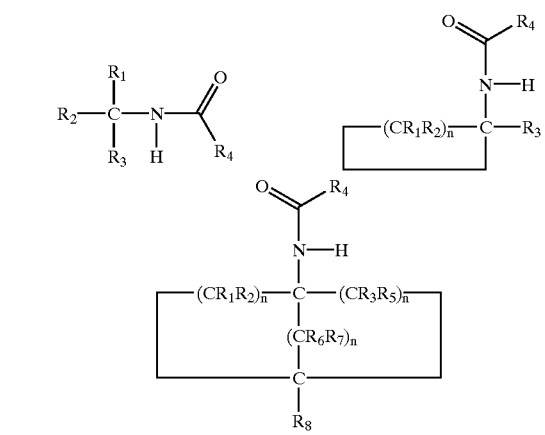

wherein the groups R$_1$, R$_2$, R$_3$, R$_4$, R$_5$, R$_6$ and R$_7$ are independently selected from hydrogen, alkyl, substituted alkyl, cycloalkyl, substituted cycloalkyl, aryl, substituted aryl and where any of the groups R$_1$, R$_2$, R$_3$, R$_4$, R$_5$, R$_6$ and R$_7$ is an alkyl, cycloalkyl or aryl substituent, the group optionally including one or more substituents or heteroatoms and the n values are independently integers in the inclusive range from 1 to 8.

* * * * *